United States Patent [19]
Mills

[11] Patent Number: 4,815,447
[45] Date of Patent: Mar. 28, 1989

[54] MOSSBAUER CANCER THERAPY

[76] Inventor: Randell L. Mills, R.D. 2, Cochranville, Pa. 19330

[21] Appl. No.: 713,448

[22] Filed: Mar. 19, 1985

[51] Int. Cl.$^4$ ............................................. A61N 5/12
[52] U.S. Cl. ...................................... 600/1; 128/1.3; 128/654; 378/3; 378/65; 424/9
[58] Field of Search ...................... 378/3, 65; 128/1.1, 128/1.3, 654; 424/9; 250/833; 604/20

[56] References Cited

U.S. PATENT DOCUMENTS

| | | | |
|---|---|---|---|
| 3,057,998 | 11/1962 | West | 128/1.1 |
| 3,257,558 | 6/1966 | Cook et al. | 250/83.3 |
| 3,612,875 | 10/1971 | Ord | 378/3 |
| 3,631,247 | 3/1969 | Barton, Jr. | 378/3 |
| 3,781,562 | 12/1973 | Singh | 378/3 |
| 3,794,840 | 2/1974 | Scott | 378/65 |
| 4,059,769 | 11/1977 | Alexandrov et al. | 250/493.1 |
| 4,446,568 | 5/1984 | Williams et al. | 378/3 |
| 4,485,086 | 11/1984 | Wong | 424/1.1 |
| 4,516,535 | 5/1985 | Russell, Jr. et al. | 128/1.1 |

FOREIGN PATENT DOCUMENTS 0198257 3/1986 European Pat. Off. .
WO85/01871 4/1985 World Int. Prop. O. .

OTHER PUBLICATIONS

2389 Medical Physics, vol. 12, No. 4, Jul./Aug. 1985, pp. 532–536, New York, "Photon Activation Therapy".
Nuclear Instruments and Methods, vol. 155, No. 1/2, Sep. 1978, pp. 97–101, North Holland Publishing Co., "High Field Mossbauer Spectrometer Using Bitter Magnets".
8164 Instruments and Experimental Techniques, vol. 24, No. 5, part 1, Sep.–Oct. 1981, pp. 1151–1153, Plenum Publishing Corp., New York, U.S. S. M. Irkaev et al, "Isomer-Shift Compensation with Resonance Detectors in Mossbauer Spectroscopy".
2107B Nuclear Instruments & Methods, section B14, No. 3, Mar. 1986, pp. 323–340, Elsevier Science Publishers B.V., Holland J. G. Mullen et al. "Cold Moving Mice: a Microfoil Internal Conversion Electron Detector for Low and Intermediate Energy Mossbauer Transitions".

*Primary Examiner*—C. Fred Rosenbaum
*Assistant Examiner*—Mark F. Colosimo
*Attorney, Agent, or Firm*—Weingarten, Schurgin, Gagnebin & Hayes

[57] ABSTRACT

Frequency selective radiation therapy providing selective tissue damage or necrosis by irradiating a component element of the target tissue at the corresponding Mossbauer absorption frequency. The component radiation absorption at the Mossbauer absorption frequency is thus enhanced many times over the absorption of the surrounding tissue having a different Mossbauer absorption frequency. The energy thusly absorbed by the target tissue component is converted to and remitted as Auger electrons, which provide intranuclear radiation resulting in lethal double strand breaks in the DNA molecules of the target tissue. The therapy is administered in frequency and tissue selective modes of treatment, and may be combined with conventional chemotherapeutic agents to provide a further enhanced treatment modality. Moreover, the source frequency can be adjusted to enhance the killing effect. The therapy method and apparatus according to the present invention is useful in combination with naturally occurring or administered pharmaceutical stable isotope absorbers, having significantly reduced side effects by comparison to convention chemotherapy or radiation therapy.

11 Claims, 1 Drawing Sheet

MOSSBAUER CANCER THERAPY

FIELD OF THE INVENTION

The present invention relates to therapeutic method and apparatus, and specifically to frequency selective radiation therapy for cancer.

BACKGROUND OF THE INVENTION

In the treatment of tumors by ionizing radiation, x-rays or gamma rays are particularly used. The ideal in radiation therapy of malignant disease is achieved when the tumor is completely eradicated and the surrounding normal tissue, in the treated volume, shows little or no evidence of structural or functional injury. The important factor in successful treatment is the difference in radiosensitivity of neoplastic and normal cells. All tissues, normal and neoplastic, are affected by radiation so that radiosensitivity is a relative term. The basis of radiation therapy is that cells that are actively proliferating or that are of a primitive type are more sensitive than normal tissue so that there is usually a considerable margin between doses that are damaging to neoplastic and to normal cells. The difference depends on the capacity for intracellular repair of normal and neoplastic cells and the ability of normal organs to continue to function well if they are only segmentally damaged. If surrounding tissue can tolerate twice the radiation dose of a given tumor, then the tumor is radiosensitive.

Mammalian cells are capable of accumulating radiation damage before they are killed exponentially. Also, if allowed sufficient time after exposure, mammalian cells are capable repairing sublethal and potentially lethal radiation damage. The effects of x-rays of gamma rays on growing cells vary with intensity and duration of exposure and consist of destruction of some cells, inhibition of imminent mitosis; followed by abnormal mitosis and disruption of the cells and damage to resting cells so that continued proliferation fails. The prime target of present radiotherapy is the DNA molecule of a cell which does not select for cancer cells but selects for DNA repair capabilities. Even a two-to-one increase in radiation sensitivity in cancer cells will result in a curable condition. However, normal surrounding tissue may not be more tolerant to x-ray therapy than cancer tissue which makes this therapeutic modality useless.

SUMMARY OF THE INVENTION

Mossbauer absorption, which is the resonant absorption of gamma rays by nuclei, represents a method of increasing the radiosensitivity of tumors in terms of orders of magnitude via selective energy deposition in cancer cells. Mossbauer radiation is completely analogous to optical absorption. In the latter, the ultimate source of radiation consists of excited atoms or molecules wich decay to the ground state. The radiation after being suitably monochromatized by a prism or diffraction grating is incident upon the sample and the intensity of the beam which is transmitted through the sample (absorber) varies as a function of the frequency as photons of energy equivalent to electronic, vibrational, rotational, and translational transitions are absorbed. In Mossbauer absorption, the source comprises excited nuclei which is decaying to their ground state emit gamma radiation; with certain nuclei in appropriate surroundings, such as exist in a crystal lattice, the radiation is highly monochromatic. In fact, the gamma-ray line can be so narrow that its frequency may be shifted significantly by incorporating the source or absorber in a mass driver oscillating at moderate velocities to produce a Doppler effect. The frequency of the mass driver which provides a Doppler shift to the gamma ray photons functions analogously to the dispersion device in optical absorption. By varying the driving frequency, a resonance system can be driven by the emitted gamma photons and the nuclear energy transitions of the sample (absorber). The absorber may occur naturally, or as in the preferred embodiment, comprise added stable pharmaceutical isotopes, discussed below.

Furthermore, since it has been determined that cancer cells differ from normal cells with respect to level of aerobic versus anaerobic metabolism, internal concentrations of ions such as $Ca^{2+}$ and $Mg^{2+}$, pH, spin lattice relaxation times, and resting membrane potentials, it is believed that such differences would cause differences in the nuclear microenvironment in cancer cells versus normal cells significant enough to result in excitation energy differences on the order of $10^{-6}$ eV. Such excitation differences will affect Mossbauer absorption, and would allow for selective targeting of cancer cells. For example, exposing malignant tissue with an Fe-57 absorber to a narrow line width beam of 14.4 KeV photons having a photon energy equal to the Fe-57 nuclear transition of Cytochrome c (in this tissue), which is different from normal tissue transition and therefore represents a powerful treatment modality.

BRIEF DESCRIPTION OF THE DRAWING

These and other features of the present invention will be further understood by reading the following detailed description, taken in combination with the FIGURE, showing one embodiment of the apparatus according to the present invention.

DETAILED DESCRIPTION OF THE INVENTION

Figure 1:
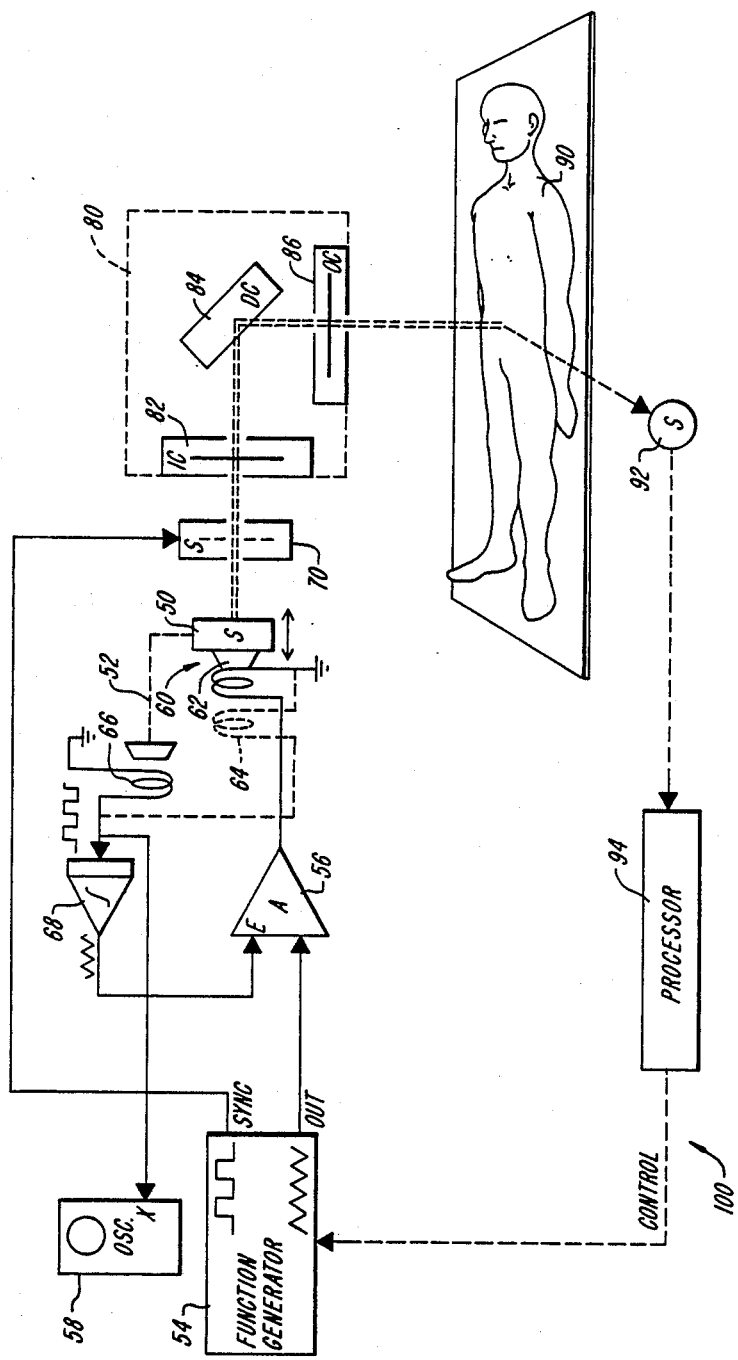

The most dramatic killing effect of radiation has been shown to be due to intranuclear radiation effects of internal conversion and Auger electrons which result in lethal double stranded breaks in DNA molecules. Commerford, S. L.; et al., Int. J. Radiation Biol., (1980), 37, p. 547; Linz, U., et al., "7th Intenational Congress of Radiation Research," Amsterdam, 1983. Internal conversion results in the ejection of inner shell electrons. The difference between the ionization energy of the inner shell electron and that of the outer shell is released either in the form of a fluorescence x-ray photon or is transmitted to another electron which is then ejected as an Auger electron. The process continues, shell by shell, until the valence shell is reached and thus leads to multiple ionizations of the atom. Such a valency cascade is known as the Auger effect. For elements of low or medium atomic number, the Auger electrons have energies up to a few KeV with a relatively high linear energy transfer (LET) of 1 to 10 ev/nm. Since such electrons dissipate their energy in materials of unit density within a distance of the order of 10 to 100 nm, they may efficiently damage molecules in the nearness of the decay event.

Mossbauer absorption depends on the microelectronic environment of the nucleus. The energies of the nuclear transitions of the absorber are dependent on the S electron density, electric field gradient, and effective magnetic field at the position of the nucleus in which resonant gamma ray absorption occurs. For example, resonant absorption by $^{57}$Fe is affected by the bonding in the iron ligand complex and factors which affect this bonding such as pH, ionic strength, ionic charge of the central atom, concentration of ions such as $Mg^{+2}$ and $Ca^{+2}$ as well as electric and magnetic fields.

Mossbauer nuclei absorb gamma radiation and are excited to a high energy nuclear state. Following non-recoiling absorption, the predominant mode of decay is by internal conversion. For example, following resonant absorption of the incident gamma ray the excited $^{119}$Sn nuclei in the absorber undergo internal conversion 84 percent of the time. In a paper by Yagnik, C. M.; Makak, R. A.; Collins, R. L., (1974) Nuclear Instrumentation Methods, 114, p. 1, 84, 20 KeV internal conversion and 75, 3 KeV Auger electrons are re-emitted for every 100 gamma rays resonantly absorbed. Approximately half of these electrons are emitted in the backward direction, which is not the case with particle radiation. The remainder of exicted nuclei re-emit gamma or x-rays. Thus, Mossbauer cancer therapy promises the advantages of selective radionucleotides without systemic radiation of normal tissue, higher kill per event secondary to production of Auger electrons, and higher kill per atom due to the fact that once a Mossbauer absorber atom decays it will be re-excited with probability equal to the original excitation event.

Momentum and energy are conserved during an emission event. For a free atom of mass M, the recoil energy due to emission of a photon of energy $E_o$ is $E_o^2/2Mc^2$, where c is the velocity of light. If the atom is in motion during emission, the photon energy will be modified by a term $E_o|V/c|\cos\sigma$, where V is the velocity of the atom and $\sigma$ is the angle between V and the momentum vector of the photon. The energy of the photons emitted by such atoms is given by (emission)

$$E\gamma = Eo - Eo^2/2Mc^2 + E_o|V/c|\cos\sigma \quad (1)$$

where $E_o$ is the photon energy in the rest frame of the nucleus. The photon energy for resonant absorption by a similar nucleus moving with velocity V' and direction $\sigma'$ is (absorption):

$$E'\gamma = Eo + Eo^2/2Mc^2 + Eo(V'/c)\cos\sigma' \quad (2)$$

The energy of gamma rays emitted by a system of free atoms moving with thermal velocities would be centered at $E_o - E_o/2Mc^2$ while the resonant absorption cross-section would be centered at $E_o + E_o/2Mc^2$. Thus, resonant absorption would be expected to occur for the fraction of events represented by the overlap in energy of the emission and absorption lines. The width of this overlap region is of the order of thermal energy: about $10^{-2}$ eV at room temperature. If the atom is in a bound state, a deviation from Equations 1 and 2 is observed. Mossbauer discovered that a certain fraction of gamma rays emitted by Ir-191 nuclei in a solid do not obey Equation 1; instead, they had energy equal to $E_o$ and a line width $\Gamma = \hbar/T_m$, where $T_m$ is the mean life of the excited state; corresponding effects were observed in absorption. The significant fact is that the emitting (or absorbing) atom is bound to other atoms in a solid. There then exists a certain probability that the recoil momentum associated with the emission (or absorption) of a photon will be taken up by the lattice rather than by the individual atom. When this occurs, the recoil energy $E_o/2Mc^2$ becomes vanishingly small because M is now essentially the mass of the crystal rather than the mass of a single atom. In addition, the lattice has a discrete set of vibrational transitions. This means that the last term in Equation 1 or 2 is replaced by a quantity which describes the number of phonons that have been interchanged between the lattice and the gamma ray phonons. There is a nonvanishing probability that no photons are exchanged. When these conditions prevail, the emission (or absorption) is described as "recoilless" or "recoil-free," and emitted (or absorbed) photons match very closely the energy and level widths of the nuclear transition. This feature characterizes the Mossbauer effect, which is applied for therapeutic treatment according to the present invention.

The probability of a recoilless event (emission or absorption) depends on certain properties of the solid as well as the energy and mean life of the nuclear excited state, the solid need not be crystalline. Mossbauer effects have been observed in amorphous materials and even liquids of high viscosity. If f is the probability of a recoilless event, also known as the Debye-Waller factor, it has been shown that $$f = \exp\left(\frac{-4\pi^2 <r^2>}{\lambda^2}\right) \quad (3)$$

where $<r^2>$ is the square of the displacement of the emitting or absorbing atom from its equilibrium position along the direction of the gamma ray momentum, averaged over the lifetime of the nuclear excited state; $\lambda$ is the wavelength of the radiation. It can be seen from Equation 3 that f is large when the scattering center is confined to a region small with respect to the wavelength of the radiation involved. $<r^2>$ decreases with increasing lattice binding energy; it also decreases as the temperature is lowered.

The Debye-Waller factor has been calculated for a crystal in which the forces are harmonic, using the Debye model of a solid:

$$f = \exp\left\{-3/2\, E_0^2/2Mc^2 \cdot 1/K\sigma\left[1 + 2/3\left(\frac{\pi T}{\sigma}\right)^2\right]\right\} \quad (4)$$

in which T is the Debye temperature, M is the atomic mass, K is the Boltzmann constant, and $E_o$ is the gamma ray energy. The recoil energy in the case of Fe-57 used as an absorber pharmaceutical is $2\times10^{-3}$ eV; this is well below the average vibrational energy at room temperature ($\sim 10^{-2}$ eV). The low recoil energy coupled with relatively high Debyte temperatures for iron complexes (e.g., $\sigma = 355°$ C. for Fe metal) makes Fe-57 particularly suitable for Mossbauer absorption. The Debye-Waller factor for Fe-57 in metallic iron is 0.7 at room temperature.

In the low temperature limit $$f = \exp\left[-3/2\frac{E_0/2Mc^2}{K\sigma}\right] \quad (5)$$

It can be seen from Equation 5 that when the free atom recoil energy is less than $K\sigma$, which is the average energy of a lattice vibrational mode, a recoil-free event has a high probability of occurring. At 5° K., the value of f in oxyhemoglobin has been found experimentally to be 0.83. The recoil energy due to absorption of a 14.4 KeV photon by hemoglobin is $2\times10^{-6}$ eV; the recoil energy of cytochrome c embedded in a protein matrix would be expected to be less; thus, it would more closely approach the line width.

The absorption cross section for a gamma ray to produce a transition between nuclear ground and excited states at resonance follow by internal conversion is given by $$\sigma = \frac{1}{2\pi} \frac{h^2 c^2}{E_o^2} \frac{2Ie + 1}{2Ig + 1} \frac{\alpha}{1 + \alpha} \quad (6)$$

where h is Planck's constant, c is the velocity of light, $E_o$ is the transition energy, Ie and Ig are the excited and ground state spins RLM, respectively, and $\alpha$ is the internal conversion coefficient ($\alpha$ describes the relative strength of radiative (gamma ray) and nonradiative (electron conversion) processes connecting the ground and excited states; $\alpha = 0$ if all the decays from the excited state involve the emission of a gamma ray). The fact that this cross-section is dependent entirely on nuclear parameters is an important and useful feature of the Mossbauer effect. For a single $Fe^{57}$ nucleus, $\sigma_o$ has the value $2.2 \times 1.^{-17}$ cm$^2$ for the 14.4 KeV transition. The cross section is about $10^7$ times larger than the actual geometrical cross-section of the nucleus and is also very large compared to the photoelectric (electronic) absorption cross-section for iron, which is $5.5 \times 10^{-21}$ cm$^2$ per atom at this energy. The absorption is an exponential function of the cross-section; thus, the nuclear resonance absorption process is a strong effect.

THE APPARATUS

The overall operation of the system may be described as follows: the radioactive source in the form of a thin film of nonmagnetic material such as stainless steel, copper, or palladium into which radioactive Co-57 has been allowed to diffuse produces a beam of highly homogeneous photons having an average energy of 14.4 KeV. The homogeneity, or line width $\Delta E$ is $4.5 \times 10^{-9}$ eV so that $\Delta E/E$ is less than $10^{-12}$. A filter selects the 14.4 KeV photon from the other two photons of different energy.

By mounting the source on an accurately controlled mass drive, the energy of the photon is shifted by means of the Doppler effect. A velocity of 1 mm/sec corresponds to an energy change of $4.8 \times 10^{-8}$ eV or more than ten line widths. A wide variety of velocity drives exist. The arrangement 100 shown in FIG. 1 is one in which the source 50 is mounted on a cone 62 of a speaker 60 and the speaker is driven so that a constant velocity is linearly achieved. A symmetric triangular wave form of approximately 5 Hz. Since the displacement of the speaker coil is quite closely proportional to the input voltage, it is necessary to provide a ramp voltage in order to produce a constant velocity. This is accomplished by a triangular wave. A function generator 54 is employed to produce an accurate, low frequency triangular voltage. This voltage is applied to the speaker 60 through a power amplifier 56. In practice, it is necessary to employ considerable negative feedback to produce an accurate constant velocity. This is accomplished by coupling a second (or using a double voice coil 64) speaker 66 to the drive speaker 60 with a rigid rod 52, and providing the error signal from the second speaker (monitored by oscilloscope 58) to the amplifier 56 through the integrator 68 as shown schematically in FIG. 1. The source 50 is mounted on the rod connecting the two speakers.

Since the source executes two velocity excursions, one at positive and one at negative accelerations, a synchronized shutter 70 can be used to block radiation during the nonresonant excursion.

The source, or emitter of radiation, can also include the techniques known to Mossbauer spectrometry, with the addition of a single frequency filter 80. The filter 80, receives source 70 radiation through an input collimator 82 and enters a diffraction crystal 84. Since the diffraction angle can be calculated (Bragg equation $n\lambda = 2d \sin \theta$), the desired frequency is selected by placement of a second output collimator 86 and the selection of a crystal having an appropriate intranuclear layer distance (d).

In addition to the above-mentioned photon sources, the photon emitters of Table 1 listed further below are useful in conjunction with absorbers having the listed corresponding absorption frequencies.

Fluorescence, or nuclear emissions of the tissue components excited at the Mossbauer frequency can also be observed from the target area. The dynamic range (signal-to-noise) can be enhanced by viewing the subject 90 off-axis from the incident radiation from the source, thereby eliminating the background level (from the source). Off-axis viewing is possible due to the nondirectional characteristic of the fluorescence of the target tissue component at the Mossbauer frequency. Moreover, the frequency of the fluorescence will coincide with the frequency of the source due to the narrow spectrum of the Mossbauer resonance.

Furthermore, the fluorescence can be continuously monitored by sensor 92 to give a characteristic plot of the treatment effectiveness. A control signal can be derived from such fluorescence, and combined or processed by processor 94 according to the characteristic plot to continuously control the source to optimize the therapy treatment.

IMAGE SCANNING

All Mossbauer isotopes are gamma emitters following absorption of the same energy gamma photon, and most are stable isotopes; therefore, they can be used in scintiscans. As in the case of radionuclides, information can be gained based on differential uptake, excretion, or concentration as a consequence of the physiology of the pathological process. But Mossbauer scintiscans also provide the ability to diagnose disease processes and to selectively image different tissues based on the phenomenon of the differential resonance frequency of the absorber isotope in different tissue environments. Exciting the absorber isotope or isotopes by causing a selected Doppler shifted emission from the emitter or emitters along one axis and simultaneously scanning with conventional scintiscan instrumentation along an axis different from the former axis produces a Mossbauer Isotopic Resonant Absorption of Gamma Emission (MIRAGE) scintiscan. Due to attenuation of the exciting beam as a function of distance along the emitting axis, a correction algorithm has to be used to process the data to produce an image of the actual distribution of the Mossbauer isotope or isotopes in the tissue.

Presently, radionucleotides which have short half lives, on the order of hours, and which are gamma-emitting isotopes, are used in scintiscans to gain diagnostic information based on the physiological properties of the pathological process. These properties include differential uptake, concentration, or excretion of the radionucleotide by normal versus diseased tissue. For example, hepatic scintiscans are performed with gamma-emitting isotopes that are extracted selectively by the liver, followed by external radiation scanning of the upper abdomen. There are basically three types of liver scans: the colloidal scan, which depends on uptake of labelled colloid by Kupper cells, where $^{198}$Au colloidal gold or $^{99m}$Tc sulfur colloid is most commonly used; the HIDA or PIPIDA scans ($^{99m}$Tc-labelled N-substituted iminoacetic acids) in which the dye is taken up and excreted by hepatocytes, and the gallium scan, in which the radionuclide $^{67}$Ga is concentrated in neoplastic or inflammatory cells to a greater degree than in hepatocytes. Hence, a hepatoma or liver abscess will produce an area of reduced uptake or "hole" using colloid or HIDA or PIPIDA scans, but there will be an area of increased uptake or "hot spot" with a gallium scan. The gallium scan is also helpful in diagnosing neoplastic infiltration in the patient with cirrhosis, since the tumor will show increased uptake, while fibrous bands will show decreased uptake. Another major application of HIDA or PIPIDA liver scans is in the diagnosis of acute cholecystitis, where failure of the nuclide to enter the gall bladder is considered evidence of cystic duct or common bile duct obstruction. The normal physiology involved is the uptake of these compounds by the hepatocytes followed by excretion into the biliary canaliculi and concentration in the gall bladder.

PHARMACEUTICALS

A number of pharmaceutical isotopes show the Mossbauer effect and a change of absorption frequency in tissue. The stable isotope Fe-57 demonstrates this effect; thus, cytochrome c which contains Fe can be selected as a target for Mossbauer absorption. Cytochrome c is a heme protein found in the mitochrondria of mammalian cells. It constitutes about 1 wt% of mitochrondrial protein (*Journal of Bioenergetics and Biomem. Vol.* 16, Numbers 5/6, Dec., (1984), p. 428), and is involved in the respiration of aerobic organisms and tissues. It has a molecular weight between 12,000 and 13,000 and one heme group per molecule. At least three bonds link the heme to the protein in cytochrome c; one is thought to be an iron protein bond and two are covalent bonds to the porphyrin ring.

To obtain Fe-57 in the proper excited state, it is necessary to use the radioactive isotope Co-57 which decays with a half life of 270 days, to the 136 KeV excited state of Fe-57; the latter nucleus in decaying to its own ground state emits three gamma rays, one of which has an energy of 14.4 KeV which has the characteristics suitable for Mossbauer absorption.

In Fe-57, the 14.4 KeV level has a mean life of $1.0\times10^{-7}$ sec of a line width of $4.5\times10^{-9}$ eV, so that when Co$^{57}$ is embedded in a nonmagnetic solid, the 14.4 KeV photons have a special homogeneity of three parts in $10^{-13}$. As a consequence, hyperfine interactions as small as $10^{-8}$ eV become accessible to selective absorption by Mossbauer effects. Furthermore cytochrome c is strongly bound to a heavy molecule which is embedded in a protein matrix and thus is accessible as a target by this effect.

Furthermore, iron occurs in a distinct environment (or prosthetic group) in several molecules, e.g., the heme group occurs in hemoglobin, myoglobin, peroxidases, and catalases as well as in cytochromes. In addition, many biological molecules contain Fe at their active centers. Thus, the potential of using this isoptope as a target of therapy is not limited to cytochromes. For example, spectra of red blood cells demonstrate that the absorption spectrum of deoxyhemoglobin is significantly different from that of oxyhemoglobin. This property may be used to treat large tumors which have outgrown their blood supply and are therefore ischemic. By irradiating at the deox Hb Doppler frequency, the gamma rays would be selectively absorbed by red blood cells present in vessels supplying the tumor. Coagulation secondary to damage to those cells would result in thrombosis of the blood supply to the tumor and concomitant tumor death.

Fe-57 occurs with a natural abundance of 2.2%. Furthermore, the total body iron stores are about 4 g and the turnover rate is about 1 mg/day. Patients who consume Fe-57 would incorporate this isotope in cells which have a rapid turnover rate. Cancer cells would be enriched relative to normal cells.

Many other stable isotopes demonstrate recoilless absorption of gamma ray photons following recoilless emission from the corresponding decaying isotope. The absorber isotopes appear in Table 1. The isotopes $^{57}$Fe, $^{83}$Kr, $^{119}$sn and $^{162}$Dy have large Mossbauer cross-sections and isotopes of Fe, Sn, Sb, I, Eu, and Dy are, in particular, very suitable for cancer pharmaceuticals.

TABLE 1

| Absorber | Source(s) |
|---|---|
| $^{176}$Yb | $^{176}$Tm |
| $^{159}$Tb | $^{159}$Gd $^{159}$Dy |
| $^{165}$Ho | $^{165}$Dy $^{165}$Yb $^{165}$Er |
| $^{231}$Pa | $^{231}$Th $^{231}$U |
| $^{157}$Gd | $^{157}$Eu $^{157}$Tb |
| $^{164}$Er | $^{164}$Ho $^{164}$Tm |
| $^{168}$Er | $^{168}$Ho $^{168}$Tm |
| Tc$^{99}$ | Mo$^{99}$ |
| Gd$^{156}$ | Eu$^{156}$ Tb$^{156}$ |
| Gd$^{154}$ | Eu$^{154}$ Tb$^{154}$ |
| Er$^{167}$ | Ho$^{167}$ Tm$^{167}$ |
| $_{68}$ER$^{170}$ | Ho$^{170}$ Tm$^{170}$ |
| Sm$^{152}$ | Pm$^{152}$ Eu$^{152m}$ Eu$^{152}$ |
| Hf$^{176}$ | Lu$^{176m}$ Ta$^{176}$ Lu$^{176}$ |
| Tm$^{169}$ | Er$^{169}$ Yb$^{169}$ |
| U$^{238}$ | Pu$^{242}$ |
| Sm$^{151}$ | Pm$^{151}$ |
| Sm$^{153}$ | Pm$^{153}$ |
| $_{62}$Sm$^{154}$ | Pm$^{154}$ Eu$^{154}$ |
| Pr$^{141}$ | Ce$^{141}$ Nd$^{141}$ |
| Os$^{186}$ | Re$^{186}$ Ir$^{186}$ |
| Os$^{188}$ | Re$^{188}$ Ir$^{188}$ |
| Hf$^{177}$ | Lu$^{177m}$ Ta$^{177}$ Lu$^{177}$ |
| Lu$^{175}$ | Yb$^{175}$ Hf$^{175}$ Hf$^{177m}$ |
| Gd$^{160}$ | Eu$^{160}$ |
| Hf$^{178}$ | Lu$^{178}$ Ta$^{178}$ Hf$^{178m}$ |
| Gd$^{158}$ | Eu$^{158}$ Tb$^{158}$ |
| Er$^{166}$ | Ho$^{166m}$ Tm$^{166}$ Ho$^{166}$ |
| Cs$^{133}$ | La$^{133}$ Ba$^{133}$ Xe$^{133}$ |
| $^{174}$Yb | $^{174m}$Tm $^{174}$Lu $^{174}$Tm |
| $^{67}$Zn | $^{67}$Cu $^{67}$Ga |
| $^{172}$Yb | $^{172}$Tm $^{172}$Lu |
| $^{171}$Yb | $^{171}$Tm $^{171}$Lu |
| $^{170}$Yb | $^{170}$Tm $^{170}$Lu |
| $^{131}$Xe | $^{131}$I $^{131}$Cs $^{131}$Xe |
| $^{186}$W | $^{186}$Ta $^{186}$Re |
| $^{184}$W | $^{184}$Ta $^{184m}$Re $^{184}$Re |
| $^{183}$W | $^{183}$Ta $^{183}$Re |
| $^{182}$W | $^{182}$Ta $^{182}$Re |
| $^{180}$W | $^{180m}$Ta $^{180}$Re $^{180}$Ta |
| $^{232}$Th ($^{228}$Ra) | $^{236}$U |
| $^{181}$Ta | $^{181}$Hf $^{181}$W |
| $^{125}$Te | $^{125}$Sb $^{125}$I $^{125m}$Te |
| $^{147}$Nd | $^{147}$Pm $^{147}$Nd |
| $^{149}$Sm ($^{145}$Nd) | $^{149}$Pm $^{149}$Eu |
| $^{101}$Ru | $^{101}$Tc $^{101m}$Rh $^{101}$Rh |
| $^{99}$Ru | $^{99}$Tc $^{99m}$Rh $^{99}$Rh |
| $^{195}$Pt | $^{195m}$Ir $^{195}$Au $^{195}$Ir $^{195m}$Pt |

TABLE 1-continued

| Absorber | Source(s) |
|---|---|
| $^{147}$Pm ($^{147}$Sm) | $^{147}$Nd |
| $^{189}$Os | $^{189}$Re $^{189}$Ir $^{189m}$Os |
| $^{237}$Np ($^{233}$Pa) | $^{237}$U $^{241}$Am $^{237}$Pu |
| $^{61}$Ni | $^{61}$Co $^{61}$Cu |
| $^{83}$Kr | $^{83}$Br $^{83}$Rb $^{83m}$Kr |
| $^{193}$Ir | $^{193}$Os $^{193}$Pt |
| $^{191}$Ir | $^{191}$Os $^{191}$Pt |
| $^{201}$Hg | $^{201}$Au $^{201}$Ti |
| $^{180}$Hf | $^{180}$Lu $^{180m}$Ta $^{180}$Ta |
| $^{139}$La | $^{139}$Ba $^{139}$Ce |
| $^{187}$Re | $^{187}$W |
| $^{234}$U | $^{234m}$Pa $^{238}$Pu $^{234}$Np $^{234}$Pa |
| $^{239}$Pu | $^{239}$Np $^{243}$Cm $^{239}$Am |
| $^{190}$Os | $^{190}$Re $^{190}$Ir $^{190m}$Os |
| $^{197}$Au | $^{197}$Pt $^{197}$Hg |
| $^{160}$Dy | $^{160}$Tb $^{160}$Ho |
| $^{155}$Gd | $^{155}$Eu $^{155}$Tb |
| $^{73}$Ge | $^{73}$Ga $^{73}$As |
| $K^{40}$ | $^{39}$K(a,y) $^{40}$K |
| Am$^{243}$ | Pu$^{243}$ Bk$^{247}$ |
| $^{145}$Nd | $^{145}$Pr $^{145}$Pm |
| $^{153}$Eu | $^{153}$Sm $^{153}$Gd |
| $^{129}$I ($^{129}$Xe) | $^{129m}$Te $^{129}$Te $^{129m}$Xe |
| $^{119}$Sn | $^{119m}$In $^{119}$Sb $^{119}$In $^{119m}$Sn |
| $^{57}$Fe | $^{57}$Mn $^{57}$Co |
| $^{151}$Eu | $^{151}$Sm $^{151}$Gd |
| $^{129}$Xe | $^{129}$I $^{129}$Cs $^{129m}$Xe |
| $^{164}$Dy | $^{164}$Tb $^{164}$Ho |
| $^{57}$Fe | $^{57}$Mn $^{57}$Co |
| $^{161}$Dy | $^{161}$Tb $^{161}$Ho |
| $^{162}$Dy | $^{162}$Tb $^{162}$Ho |
| $^{117}$Sn | $^{117m}$Sn $^{117m}$In $^{117}$Sb |
| $^{121}$Sb | $^{121m}$Sn $^{121}$Sn $^{121m}$Te $^{121}$Te |
| $^{127}$I | $^{127}$Te $^{127}$Xe |
| $^{133}$Ba | $^{133}$La $^{133m}$Ba |
| $^{145}$Pm | $^{145}$Sm |
| $^{147}$Sm | $^{147}$Pm $^{147}$Eu |

These Mossbauer isotopes could be used to replace the same element, e.g., $^{127}$I and $^{129}$I could be used in hormones or $^{67}$Zn in enzymes. Also, Mossbauer isotopes could be used to substitute for a different element, e.g., $^{133}$Cs could be substituted for Na$^+$ and K$^+$ or $^{151}$Eu as $^{151}$Eu$^{2+}$ could be used as a substitute for Ca$^{2+}$ in bone. Furthermore, many possibilities exist for developing pharmaceuticals which exploit the properties of cellular structures of molecules to cause differential binding of a Mossbauer atom or molecule incorporating one or more Mossbauer atoms to selected sites in the tumor cells. Large local concentrations could be achieved through this process. $^{119}$Sn$^{2+}$ is a candidate for binding to DNA, which is negatively charged. For $^{119}$Sn, $^{119m}$Sn could be incorporated into a BaSnO$_3$ matrix to constitute the emitter. A Pd filter would remove $\beta$ particles, and the pharmaceutical could be a salt of $^{119}$Sn$^{2+}$. $^{131}$Xe or $^{129}$Xe which are membrane-soluble could be used to localize into the nuclear, mitochondrial or cellular membrane. Furthermore, experiments have shown that molecules or atoms which are dissolved into membranes or bound or absorbed to cellular structures undergo recoilless absorption. (Evan et al. 1977, Biochem. J., (1977), 166, p. 547; Giberman, E., et al., J. Phys., (1974), 35, C6-371).

TISSUE SELECTIVE THERAPY

Bone tumors and bone metastases can be treated by the incorporation of a Mossbauer absorber into bone. Recoilless absorption will occur when the isotope becomes part of the bone matrix. Emission Mossbauer nuclide for $^{133}$Cs is $^{133}$Ba. Marshall, J. H., Phys. Med. Biol., (1968), 13, p. 15 has obtained a Mossbauer spectrum with a $^{133}$CsF absorber and a source provided by $^{133}$Ba fixed onto bone powder by incubation of the latter in a solution of radioactive $^{133}$BaCl$_2$.

In addition to the alkaline earths, the rare earths are also "bone seekers." Kellershohn, C., et al., Proc. Ampere Congr. 18th, (1974), Nottingham, p. 289. Kellershohn, C., et al., J. Physique, (1979), 40, C2-505 have investigated both in vivo and in vitro fixation of rare earths onto bone material using $^{161}$Dy Mossbauer spectroscopy. Excellent spectra are obtained at room temperature indicating that the rare earth element is metabolically fixed onto the bone and is actually incorporated into a solid structure. Another pharmaceutical is $^{151}$Eu or $^{153}$Eu since both atoms can be isoelectronic with Ca$^{2+}$. $^{149}$Sm has a very significant Mossbauer cross-section of $3.7 \times 10^{-18}$ and $^{149}$Sm and $^{153}$Sm are also rare earth "bone seeking" candidates for the metabolic incorporation at sites of new bone formation secondary to metastatic or primary bone cancer.

Also, pharmaceuticals could be synthesized using these isotopes such that the Mossbauer absorption occurs at a Doppler frequency in the cancer cells which is different from that of normal cells. The difference in chemical environments between normal and cancer cells results in alternate conformation, protonation, charge, etc. of the properly constructed therapeutic molecule so that the s electron density at the Mossbauer nucleus is altered. The difference in s electron density results in a difference in the nuclear transition energy with a concomitant frequency difference of absorbed photons.

ENERGY/FREQUENCY SELECTIVE THERAPY

The Mossbauer absorption spectrum of a biopsy of normal and malignant tissue would yield the Doppler shifted frequencies that would result in selective gamma ray absorption in the malignant tissue. The apparatus and methods according to the present invention also select the source frequency to optimize the cell damage or kill when different from the actual Mossbauer absorption of the target tissue.

The photoelectric and Compton cross-sections are summarized in Table 2 which contains the mass energy absorption coefficients in the absence of the Mossbauer effects. The equation for determining the total dose from gamma ray treatment and the depth of penetration of the photons appears in the Appendix. The Appendix and Table 2 demonstrate the relationship that photons of higher energy penetrate deeper into tissue. Since the different Mossbauer isotopes demonstrate a wide range of photon energies, therapies can be designed to exploit this phenomenon to deliver the energy of the radiation to a selected depth. For example, the 14.4 KeV gamma ray of $^{57}$Fe with a mass energy tissue absorption coefficient of 1.32 cm$^2$/gm would be suitable for intraoperative radiation of breast, bowel, and pancreatic cancer, whereas the 80.65 KeV gamma ray of $^{162}$Dy with a mass energy bone absorption coefficient of 0.05 cm$^2$/gm represents a suitable isotope for the treatment of primary and metastatic bone cancer.

ALTERNATIVE COMBINATIONS OF THERAPEUTIC TREATMENTS

The two major cancer therapies are radiation therapy and chemotherapy. The latter includes agents which can be broken down into six major classes of antitumor agents, alkylating agents, antimetabolites, plant alkaloids, endocrine agents, and immunologic stimulants. Radiation and chemotherapy can be combined synergistically by synthesizing hybrid pharmaceuticals consisting of the active functional groups of chemotherapeutic agents and one or more Mossbauer nuclei per molecule. $^{195}$Pt, cisplatinum, is an example of such a hybrid molecule. Cisplatinum is an alkylating chemotherapeutic agent which becomes covalently bound to DNA. Irradiation at a distinct resonance frequency of Mossbauer nucleus, $^{195}$Pt localized in the tumor cells combines the effects of Mirage therapy with that of chemotherapy to synergistically enhance tumor cell death.

would only be relative to other cell populations in the radiation field.

The therapy according to the present invention is useful to treat disease other than cancer. The basis of therapy rests on the selective destruction of one or more cell lines. Other diseases which can be cured by elimination of specific cell lines include autoimmune diseases and transplant rejection disease, graft versus host, and host versus graft. The cellular mediators for both of these diseases are lymphocytes. The responsible cell

TABLE 2

MASS ENERGY ABSORPTION COEFFICIENTS

| Photon Energy Mev | H | C | N | O | Na | Mg | P | S |
|---|---|---|---|---|---|---|---|---|
| 0.010 | 0.00992 | 1.91 | 3.42 | 5.50 | 15.4 | 20.9 | 40.1 | 49.7 |
| .015 | 0.0110 | 0.517 | 0.916 | 1.49 | 4.43 | 6.09 | 11.9 | 15.2 |
| .020 | 0.0133 | 0.203 | 0.360 | 0.587 | 1.77 | 2.47 | 5.00 | 6.11 |
| .030 | 0.0186 | 0.0592 | 0.102 | 0.163 | 0.182 | 0.684 | 1.45 | 1.85 |
| .010 | 0.0230 | 0.0306 | 0.0165 | 0.0700 | 0.191 | 0.274 | 0.570 | 0.731 |
| .050 | 0.0270 | 0.0226 | 0.0299 | 0.0110 | 0.0996 | 0.110 | 0.282 | 0.361 |
| .060 | 0.0305 | 0.0203 | 0.0211 | 0.0304 | 0.0637 | 0.0845 | 0.166 | 0.214 |
| .080 | 0.0362 | 0.0201 | 0.0218 | 0.0239 | 0.0369 | 0.0156 | 0.0780 | 0.0971 |
| .10 | 0.0106 | 0.0213 | 0.0222 | 0.0232 | 0.0288 | 0.0331 | 0.0500 | 0.0599 |
| .15 | 0.0185 | 0.0216 | 0.0219 | 0.0252 | 0.0258 | 0.0255 | 0.0315 | 0.0351 |
| .20 | 0.0530 | 0.0267 | 0.0267 | 0.0271 | 0.0265 | 0.0277 | 0.0292 | 0.0310 |
| .30 | 0.0573 | 0.0288 | 0.0289 | 0.0289 | 0.0278 | 0.0290 | 0.0290 | 0.0301 |
| .40 | 0.0587 | 0.0295 | 0.0296 | 0.0296 | 0.0283 | 0.0295 | 0.0290 | 0.0301 |
| .50 | 0.0589 | 0.0297 | 0.0297 | 0.0297 | 0.0281 | 0.0293 | 0.0288 | 0.0300 |
| .60 | 0.0588 | 0.0296 | 0.0296 | 0.0296 | 0.0283 | 0.0202 | 0.0387 | 0.0297 |
| .80 | 0.0573 | 0.0288 | 0.0280 | 0.0289 | 0.0276 | 0.0285 | 0.0230 | 0.0287 |
| 1.0 | 0.0555 | 0.0279 | 0.0280 | 0.0280 | 0.0267 | 0.0275 | 0.0270 | 0.0280 |
| 1.5 | 0.0507 | 0.0255 | 0.0255 | 0.0255 | 0.0213 | 0.0250 | 0.0215 | 0.0251 |
| 2.0 | 0.0161 | 0.0234 | 0.0231 | 0.0231 | 0.0225 | 0.0232 | 0.0238 | 0.0235 |
| 3.0 | 0.0398 | 0.0204 | 0.0205 | 0.0206 | 0.0199 | 0.0206 | 0.0201 | 0.0210 |
| 4.0 | 0.0351 | 0.0184 | 0.0186 | 0.0187 | 0.0181 | 0.0191 | 0.0192 | 0.0199 |
| 5.0 | 0.0316 | 0.0170 | 0.0172 | 0.0174 | 0.0173 | 0.0181 | 0.0181 | 0.0192 |
| 6.0 | 0.0288 | 0.0160 | 0.0162 | 0.0166 | 0.0166 | 0.0175 | 0.0179 | 0.0187 |
| 8.0 | 0.0249 | 0.0415 | 0.0148 | 0.0151 | 0.0158 | 0.0167 | 0.0175 | 0.0181 |
| 10.0 | 0.0222 | 0.0137 | 0.0142 | 0.0117 | 0.0154 | 0.0163 | 0.0171 | 0.0183 |

| Mev | A | K | C. | Water | Air | Bone | Muscle | |
|---|---|---|---|---|---|---|---|---|
| 0.010 | 62.0 | 77.0 | 89.8 | 1.89 | 4.66 | 49.0 | 4.96 | MASS ENERGY ABSORPTION |
| .015 | 19.4 | 24.6 | 28.9 | 1.32 | 1.29 | 5.89 | 1.36 | COEFFICIENTS ($\mu_{en}$) |
| .020 | 8.31 | 10.5 | 12.5 | 0.523 | 0.516 | 2.51 | 0.514 | [cm$^2$/gm] |
| .030 | 2.46 | 3.12 | 3.75 | 0.147 | 0.107 | 0.713 | 0.151 | |
| .040 | 0.974 | 1.25 | 1.52 | 0.0617 | 0.040 | 0.305 | 0.0677 | |
| .050 | 0.184 | 0.626 | 0.761 | 0.0391 | 0.0381 | 0.158 | 0.0109 | |
| .060 | 0.281 | 0.367 | 0.413 | 0.0301 | 0.0292 | 0.0979 | 0.0312 | |
| .080 | 0.124 | 0.198 | 0.191 | 0.0253 | 0.0236 | 0.0520 | 0.0255 | |
| .10 | 0.0725 | 0.0909 | 0.111 | 0.0252 | 0.0231 | 0.0386 | 0.0252 | |
| .15 | 0.0368 | 0.0133 | 0.0188 | 0.0278 | 0.0251 | 0.0301 | 0.0276 | |
| .20 | 0.0302 | 0.0339 | 0.0367 | 0.0300 | 0.0268 | 0.0302 | 0.0297 | |
| .30 | 0.0278 | 0.0301 | 0.0319 | 0.0320 | 0.0288 | 0.0311 | 0.0317 | |
| .40 | 0.0274 | 0.0299 | 0.0308 | 0.0329 | 0.0296 | 0.0316 | 0.0325 | |
| .50 | 0.0271 | 0.0291 | 0.0301 | 0.0330 | 0.0297 | 0.0316 | 0.0327 | |
| .60 | 0.0270 | 0.0291 | 0.0301 | 0.0329 | 0.0296 | 0.0315 | 0.0326 | |
| .80 | 0.0261 | 0.0282 | 0.0290 | 0.0321 | 0.0289 | 0.0306 | 0.0318 | |
| 1.0 | 0.0252 | 0.0272 | 0.0279 | 0.0311 | 0.0280 | 0.0297 | 0.0308 | |
| 1.5 | 0.0228 | 0.0217 | 0.0253 | 0.0283 | 0.0255 | 0.0270 | 0.0281 | |
| 2.0 | 0.0212 | 0.0228 | 0.0231 | 0.0260 | 0.0231 | 0.0218 | 0.0257 | |
| 3.0 | 0.0193 | 0.0208 | 0.0213 | 0.0227 | 0.0205 | 0.0219 | 0.0225 | |
| 4.0 | 0.0182 | 0.0199 | 0.0201 | 0.0205 | 0.0186 | 0.0199 | 0.0203 | |
| 5.0 | 0.0176 | 0.0193 | 0.0200 | 0.0190 | 0.0173 | 0.0186 | 0.0188 | |
| 6.0 | 0.0175 | 0.0190 | 0.0198 | 0.0180 | 0.0163 | 0.0178 | 0.0178 | |
| 8.0 | 0.0172 | 0.0190 | 0.0197 | 0.0165 | 0.0150 | 0.0165 | 0.0163 | |
| 9.0 | 0.0173 | 0.0191 | 0.0201 | 0.0155 | 0.0141 | 0.0159 | 0.0151 | |

As an alternative to selective kill of target cells due to irradiation at a frequency which is resonant only for the isotope localized to the target cell, Mirage therapy could also be made selective by means of developing molecules or ions which are more avidly taken up by the target cells. This constraint is minimized by the relative nontoxicity of any pharmaceutical distributed in nonirradiated areas. Also, the target tissue is irradiated locally; therefore, the enhanced differential uptake lines could be selectively killed by synthesizing hybrid pharmaceuticals consisting of a protein and one or more Mossbauer isotopes. The protein binds to the surface of the target cell in a highly specific manner. A monoclonal antibody to an antigen on the cell surface or a hormone which binds to a receptor on the cell surface could serve as the protein. The tissue is irradiated at the Doppler frequency which is the resonant frequency of the absorber isotopes of the hybrid pharmaceutical molecules bound to the target cells. The subsequently released Auger electrons would destroy the target cells. Thus, the cell line responsible for disease can be eliminated without internalization of the hybrid molecule which is necessary in the case of conventional hybrid pharmaceuticals which consist of a specific binding protein and a toxin.

Modifications and substitutions of system elements by one skilled in the art are considered to be within the scope of the present invention, which is not to be limited except by the claims which follow.

APPENDIX

TOTAL ABSORBED DOSAGE: From a source of A Ci, at a constant distance of r cm., of an isotope with mean life T, where exposure occurs for durations u, starting at intervals of v and occurring n separate times on an organ of surface area S, density $\rho$ due to gamma rays emitted by the decays which have individual energies of E MeV and for which the organ's tissue have an energy absorption coefficient of $\mu_{en}$ cm/gram.

$$= A\ Ci \times 3.7 \times 10^{10} \frac{counts}{sec\text{-}Ci} \times T\ sec \times (1 - e^{-u/T}) \frac{(1 - e^{-nv/T})}{(1 - e^{-v/T})}$$

| orginal count rate at t = 0 |
| number of nuclei present at t = 0 | × | fraction of orginal nuclei that will decay during the n intervals of duration u, separation v.
| total number of decays that occur during periods of exposure |

$$\times \frac{S}{4\pi r^2} \qquad \times (1 - e^{-\mu_{en}\rho dr}) \times \qquad E\ MeV \times 1.6 \times 10^{-6} \frac{erg}{MeV} \times \frac{1}{\rho Sdr} \times \frac{1}{100}$$

| fraction of rays emitted from source that will pass through surface area, S, of organ at distance r. | fraction of ray's energy absorbed in passing through a thickness, dr, of tissue | total energy of each ray [ergs] | | |

... total number of rays that pass through the surface, S. | energy [erg] absorbed in thickness dr of tissue per photon | | ... grams of tissue in thickness dr behind surface, | S.

| | ... total energy absorbed in thickness dr from all photons | | ... total ergs absorbed per gram | total ... rads

What is claimed is:

1. A system for therapeutic administration of radiation for selective necrosis of target tissue, comprising
   a source of radiation selectively providing at least one frequency of radiation emission;
   means for tuning the frequency of said source radiation; and
   means for selective absorption of said emission administered to said target tissue, wherein
      said source is directed to provide said radiation to said target tissue and is adjusted to provide sufficient radiation at the frequency corresponding to the Mossbauer frequency of the means for selective absorption to provide target tissue necrosis, and said radiation comprises radiation applicable to Mossbauer absorption.

2. The system of claim 1, wherein said means for tuning comprises Doppler shift means.

3. The system of claim 1, wherein said filter means comprises crystal diffraction means.

4. The system of claim 1, wherein
   the excited component of said target tissue emits radiation causing necrosis of said target tissue, the apparatus further comprising
   means for detecting said target tissue radiation.

5. The system of claim 1, further comprising
   means for sensing target tissue fluorescence in response to said radiation, said fluorescence being emitted along a path off-axis from the incident radiation.

6. The system of claim 4, further comprising
   means for imaging said target tissue according to said target tissue radiation.

7. The system of claim 1, wherein
   said means for selective absorption comprises at least one of a molecule, a protein, and a peptide, wherein said means for selective absorption further includes naturally occurring and synthesized elements.

8. The system of claim 7, wherein
   said means for selective absorption comprises at least one of an isotope and a hormone.

9. The system of claim 8, wherein
   said means for selective absorption comprises a pharmaceutical.

10. The system of claim 1, further including filter means for selective transmittance of said radiation emission for providing filtered radiation.

11. The system of claim 1, wherein said radiation applicable to Mossbauer absorption comprises gamma rays.

* * * * *